(12) United States Patent
Vardi

(10) Patent No.: US 11,786,354 B2
(45) Date of Patent: Oct. 17, 2023

(54) EMBOLIC FILTER DEVICE

(71) Applicant: Gil Vardi, St. Louis, MO (US)

(72) Inventor: Gil Vardi, St. Louis, MO (US)

( * ) Notice: Subject to any disclaimer, the term of this patent is extended or adjusted under 35 U.S.C. 154(b) by 109 days.

(21) Appl. No.: 17/485,899

(22) Filed: Sep. 27, 2021

(65) Prior Publication Data

US 2022/0104932 A1 Apr. 7, 2022

Related U.S. Application Data

(60) Provisional application No. 63/086,134, filed on Oct. 1, 2020.

(51) Int. Cl.
*A61F 2/01* (2006.01)

(52) U.S. Cl.
CPC .............. *A61F 2/013* (2013.01); *A61F 2/011* (2020.05); *A61F 2230/0006* (2013.01); *A61F 2230/0065* (2013.01); *A61F 2230/0069* (2013.01)

(58) Field of Classification Search
CPC .. A61F 2/013; A61F 2/011; A61F 2230/0006; A61F 2230/0065; A61F 2230/0069; A61F 2002/016; A61F 2002/018; A61F 2/01; A61F 2/00; A61F 2/0063; A61F 2002/0068; A61F 2/0105; A61F 2/012; A61F 2/014; A61F 2002/821; A61F 2002/823; A61F 2/844; A61F 2/848; A61F 2/852; A61F 2/88; A61F 2/885; A61F 2/94; A61F 2/92

See application file for complete search history.

(56) References Cited

U.S. PATENT DOCUMENTS

| | | | |
|---|---|---|---|
| 7,252,675 B2 | 8/2007 | Denison et al. | |
| 8,494,245 B2 | 7/2013 | Liao et al. | |
| 8,591,540 B2 | 11/2013 | Boyle et al. | |
| 10,016,267 B2 | 7/2018 | Belson | |
| 2001/0044632 A1 | 11/2001 | Daniel et al. | |
| 2002/0156520 A1 | 10/2002 | Boylan et al. | |
| 2007/0005103 A1 | 1/2007 | Schaeffer | |
| 2012/0323545 A1 | 12/2012 | Aulbach et al. | |
| 2017/0042659 A1* | 2/2017 | Russell | A61F 2/013 |
| 2017/0181835 A1* | 6/2017 | Kleshinski | A61F 2/0105 |
| 2018/0055477 A1 | 3/2018 | Eskuri | |
| 2018/0271636 A1 | 9/2018 | deBeer et al. | |
| 2019/0000604 A1* | 1/2019 | Eli | A61F 2/012 |

* cited by examiner

*Primary Examiner* — Katherine M Shi
*Assistant Examiner* — Nasheha Baset
(74) *Attorney, Agent, or Firm* — David H. Chervitz

(57) ABSTRACT

An embolic filter device has a tubular structure having a front end, a first section, a first section rear end, a left collection pocket formed in the first section rear end, a right collection pocket formed in the first section rear end, a first narrow passage, a second section, a second section front end, a second section rear end, a left second section collection pocket, a right second section collection pocket, a second narrow passage, and a rear end.

14 Claims, 7 Drawing Sheets

EMBOLIC FILTER DEVICE

RELATED APPLICATION

This application claims priority to U.S. Provisional Patent Application No. 63/086,134, filed on Oct. 1, 2020, the disclosure of which is incorporated herein by reference.

BACKGROUND

This disclosure relates to a medical device and more particularly to a surgical filter device used to capture any debris generated during a transcatheter aortic valve replacement or implantation procedure.

Transcatheter aortic valve replacement (TAVR) is a surgical procedure in which a transcatheter heart valve is inserted into a vessel by use of a catheter and guided to the aorta annulus to implant the replacement heart valve. In patients who have aortic valve disease, replacement of a prosthetic aorta valve is often required to replace the damaged native valve. Minimally evasive TAVR is a technique that is an alternative to open-chest valve surgery that is used to reduce surgical trauma. TAVR is the therapy of choice for patients with severe aortic stenosis who have moderate to high surgical risk. The benefit of TAVR is attenuated by the occurrence of major disabling stroke which is associated with increased mortality and early-reduced quality of life. Despite advances in TAVR technology, stroke remains a serious complication that is associated with significant negative outcomes. The majority of these occur in the acute phase following TAVR where cerebral embolic events are frequent. The strokes are caused by debris breaking off of the original aortic valve, heart structures, and the aorta that enter the bloodstream that embolizes to the brain and other major organs such as the kidneys and the lower extremities. Cerebral embolic protection devices (CEPD) have been developed to minimize the risk of peri-procedural ischemic stroke during TAVR. CEPD have the potential to reduce intraprocedural burden of new silent ischemic injury. Additional left heart procedures, such as Mitra-clip, ablations for the treatment of arrhythmias, left atrial appendage closure, and others may cause similar debris and end organ damage.

Therefore, it would be desirable to have an embolic filter device that is capable of capturing any debris generated by the TAVR procedure that does not suffer from the limitations of prior devices or procedures. It would further be advantageous to have an embolic filter device that can filter the debris before any of the debris is capable of reaching the brain, the kidneys, any other major organs, or the lower extremities. It would also be advantageous to have an embolic filter device that may be easily manipulated or positioned by a surgeon to capture and retain any debris generated by the TAVR procedure.

SUMMARY

In one form of the present disclosure, an embolic filter device is disclosed which comprises a tubular structure having a front end, a first section, a first section rear end, a left collection pocket formed in the first section rear end, a right collection pocket formed in the first section rear end, a first narrow passage, a second section, a second section front end, a second section rear end, a left second section collection pocket, a right second section collection pocket, a second narrow passage, and a rear end.

In another form of the present disclosure, an embolic filter device comprises a tubular structure having a front end, a first section, a first section rear end, a left collection pocket formed in the first section rear end, a right collection pocket formed in the first section rear end, a first narrow passage, and a rear end.

In yet another form of the present disclosure, an embolic filter device comprises a wind sock mesh sack body having a front end ring that is expandable and collapsible, and a rear closed end.

In still another form of the present disclosure, an embolic filter device is disclosed which comprises a ball shaped body having a front opening and a mesh rear portion.

In another form of the present disclosure, an embolic filter device is provided which comprises a catheter portion having a front open end and a rear open end, a wire inserted through the catheter portion and connected to a tip portion, the tip portion having a pair of arms connected to the tip portion, and the pair of arms connected to an umbrella like mesh canopy.

In yet another form of the present disclosure, an embolic filter device has a catheter portion having a front open end and a rear open end, a wire inserted through the catheter portion and connected to a capture tip portion, the capture tip portion for capturing therein a pair of self expanding arms, the arms having a mesh canopy connected thereto.

In a further form of the present disclosure, an embolic filter device comprises a mesh central body portion having an open front end and a closed rear end, a wire connected to the closed rear end, and the open front end having a cuff.

In still another form of the present disclosure, an embolic filter device is provided having a central body portion and a pair of rings extending from a rear end of the central body portion, the rings for allowing a wire having a pair of hooked ends to be able to hook to the rings to remove the device from within a vessel.

In another form of the present disclosure, an embolic filter device comprises a mesh tubular body having an opened front end and a closed rear end, a catheter connected to the closed rear end, the opened front end having a pair of arms, with the arms for allowing a pair of hooked ends to hook on to the arms to remove the device from within a vessel.

In a further form of the present disclosure, an embolic filter device is provided having a tubular structure having a front end, a first section, a first section rear end, a left collection pocket formed in the first section rear end, a right collection pocket formed in the first section rear end, a first narrow passage, a second section, a second section front end, a second section rear end, a left second section collection pocket, a right second section collection pocket, a second narrow passage, and a rear end, and a stent having an interior, the tubular structure for insertion into the interior of the stent.

In still another form of the present disclosure, an embolic filter device is disclosed having a tubular structure having a front end, a first section, a first section rear end, a left collection pocket formed in the first section rear end, a right collection pocket formed in the first section rear end, a first narrow passage, and a rear end, and a stent having an interior, the tubular structure for insertion into the interior of the stent.

In light of the foregoing comments, it will be recognized that the present disclosure provides an embolic filter device for capturing any debris generated by the TAVR procedure.

The present disclosure provides an embolic filter device that covers the ostia of the aorta arch vessels for trapping any debris that is produced during the TAVR procedure to prevent any emboli from entering the carotid arteries.

The present disclosure provides an embolic filter device that may be collapsible and may be withdrawn from the aorta after the TAVR procedure is completed.

The present disclosure provides an embolic filter device that may be left in the aorta after the TAVR procedure is completed to continuously provide for long-term protection against any embolic events.

The present disclosure is also directed to an embolic filter device that expands or conforms to the walls of the aorta so that the device does not interfere with the TAVR procedure.

The present disclosure also provides for an embolic filter device that allows for a catheter or other device to pass through the embolic filter device and is still capable of trapping any debris.

The present disclosure is further directed to an embolic filter device which allows a wire, a catheter, or other device to pass through the embolic filter device without allowing any debris that is captured within the embolic filter device to escape.

These and other advantages of the present embolic filter device will become apparent after considering the following detailed specification in conjunction with the accompanying drawings, wherein:

DETAILED DESCRIPTION OF A PREFERRED EMBODIMENT

Figure 1:
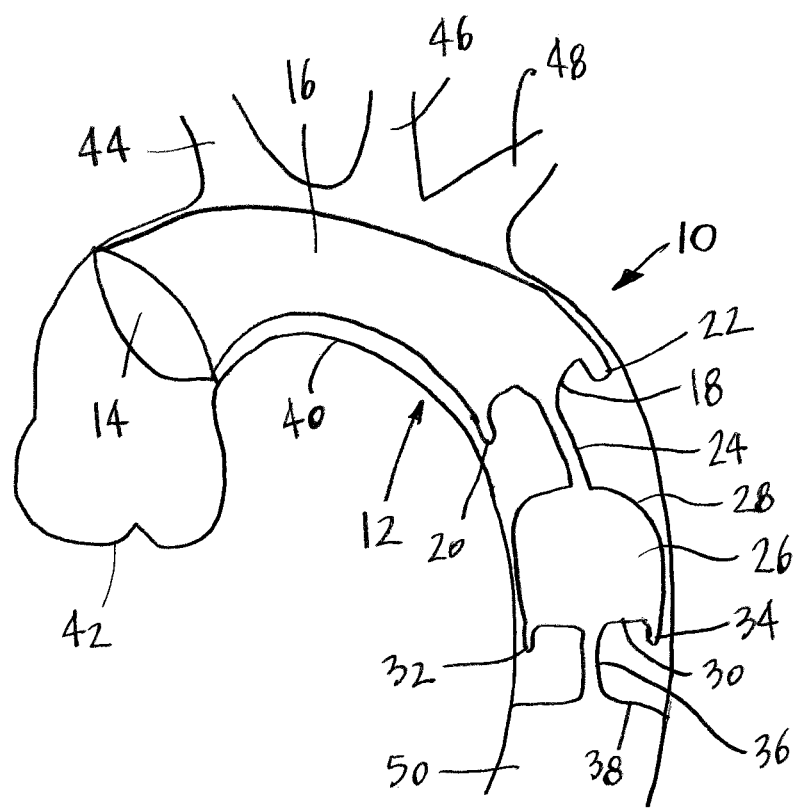
FIG. 1 is a side view of an embolic filter device constructed according to the present disclosure being deployed in an aortic arch of a patient.

Referring now to the drawings, wherein like numbers refer to like items, number 10 identifies an embolic filter device constructed according to the present disclosure. With reference now to FIG. 1, the embolic filter device 10 is shown to comprise a tubular structure 12 having a front end 14, a first section 16, a first section rear end 18, a left collection pocket 20 formed in the first section rear end 18, a right collection pocket 22 formed in the first section rear end 18, a first narrow passage or constricted section 24, a second section 26, a second section front end 28, a second section rear end 30, a left second section collection pocket 32, a right second section collection pocket 34, a second narrow passage or constricted section 36, and a rear end 38. The first narrow passage 24 and the second narrow passage 36 are closed but are capable of stretching to allow a wire, catheter, or other device to pass through the device 10. The pockets 20, 22, 32, and 34 are used to retrieve the device 10, as will be explained in detail further herein. The pockets 20, 22, 32, and 34 are also used to collect debris. Further, although the pockets 20, 22, 32, and 34 are shown it is possible to have a central pocket. The device 10 positioned within an aortic arch 40 and expands to form the shape of the arch 40. An aortic valve 42, which has replaced the original valve, is in place and any debris from the TAVR procedure will be captured by the device 10 as it flows into the device 10 through the front end 14. The first section 16 can hold a large amount of debris and the second section 14 can hold a smaller amount of debris. It is also contemplated that the sections 16 and 14 may be of equal size. The device 10 also used to cover a brachiocephalic artery 44, a left common carotid artery 46, a left subclavian artery 48, and a descending aorta 50. In this manner, the device 10 prevents any debris from entering any of the arteries 44, 46, 48, or the descending aorta 50.

The embolic filter device 10 may be constructed of any suitable material such as a polymer, a metal, or a combination of materials. The device 10 may be manufactured out of wires, threads, strings, or cords to form a mesh structure that allows blood to flow through but will be able to capture debris. As such, the device 10 may be compressible in an initial state to a small diameter product that can be inserted into the aorta through an artery. The device 10 can expand to form the shape of the aortic arch or arteries.

Figure 2:
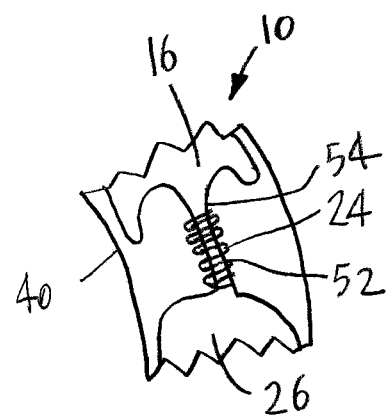
FIG. 2 is a partial perspective view of the embolic filter device shown in FIG. 1 inserted into the aortic arch of a patient with a more detailed view of a narrow passage of the embolic filter device.

FIG. 2 illustrates a partial view of the first narrow passage 24 of the device 10 positioned within the aorta arch 40. The passage 24 acts as a bottleneck that is restricted to prevent any debris to pass through but also allows a device, such as an interventional device, to pass through. The passage 24 has a spring 52 that is positioned on an outside surface 54 of the passage 24. The spring 52 constricts the passage 24 between the first section 16 and the second section 26. The spring 52 also expands to allow the passage 24 to open or expand to allow a device to pass through the passage 24. Although the spring 52 is shown, it is also possible to have a band wrapped around the outside surface 54 of the passage 24 that can expand or contract. The band may be constructed of a material which provides for expansion or contraction such as PTFE (polytetrafluoroethylene) or other similar material. It is also contemplated that the passage 24 may be woven tighter than the sections 16 and 26 and still be able to expand enough to allow a device to pass through when the device is inserted into the passage 24. The second narrow passage 36 may be formed or constructed in the same manner.

Figure 3:
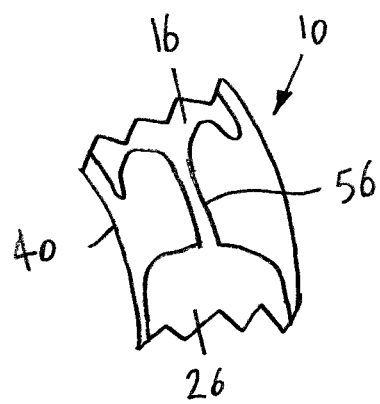
FIG. 3 is a partial perspective view of another embodiment of a narrow passage of the embolic filter device.

With reference now to FIG. 3, another embodiment of the narrow passage 56 formed between the first section 16 and the second section 26 of the device 10 is shown. The narrow passage 56 is formed by sock folding the device 10. The device 10 is also positioned within the aorta arch 40.

Figure 4:
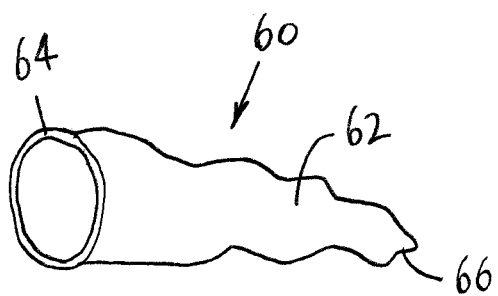
FIG. 4 is a perspective view of another embodiment of an embolic filter device constructed according to the present disclosure.

FIG. 4 depicts another embodiment of an embolic filter device 60 constructed according to the present disclosure. The embolic filter device 60 comprises a wind sock mesh sack body 62 having a front end ring 64 that is expandable and collapsible, and a rear closed end 66. The device 60 is originally configured in a collapsible state when inserted the device 60 into the aorta arch 40. Once in position, the front end ring 64 may be expanded or opened so that any debris that flows into the body 62 is captured therein and not allowed to escape due to the rear closed end 66. The mesh sack body 62 allows blood to flow through the device 60. The front end ring 64 may be formed of Nitinol.

Figure 5:
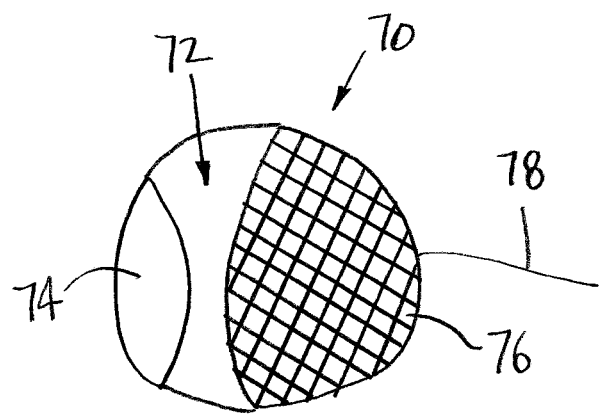
FIG. 5 is a perspective view of another embodiment of an embolic filter device constructed according to the present disclosure.

Referring now to FIG. 5, another embodiment of an embolic filter device 70 is illustrated. The embolic filter device 70 comprises a ball shaped body 72 having a front opening 74 and a mesh rear portion 76. As can be appreciated, debris and blood may flow into the front opening 74 and debris is captured by the mesh rear portion 76. Blood is allowed to flow through the device 70 and out through the mesh rear portion 76. A wire 78 is also attached to the mesh rear portion 76 to be able to retrieve the device 70 when needed. The ball shaped body 72 may be comprises of Nitinol which allows the device 70 to be introduced into the aorta arch in a collapsed state and then expanded when the position of the device 70 is confirmed within the aorta arch.

Figure 6:
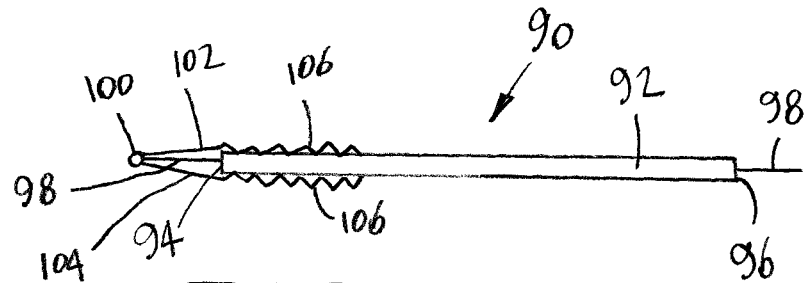
FIG. 6 is a perspective view of another embodiment of an embolic filter device constructed according to the present disclosure with the embolic filter device being shown in a collapsed state.

FIG. 6 shows another embodiment of an embolic filter device 90 constructed according to the present disclosure. The embolic filter device 90 comprises a catheter portion or wire 92 having a front open end 94 and a rear open end 96. A wire 98 is inserted through the catheter portion 92 and is connected to a tip or cap portion 100. The tip portion 100 has a pair of arms or stretchers 102 and 104 connected to the tip portion 100. The pair of arms 102 and 104 are connected to an umbrella like mesh canopy 106. The device 90 is shown in a collapsed state.

Figure 7:
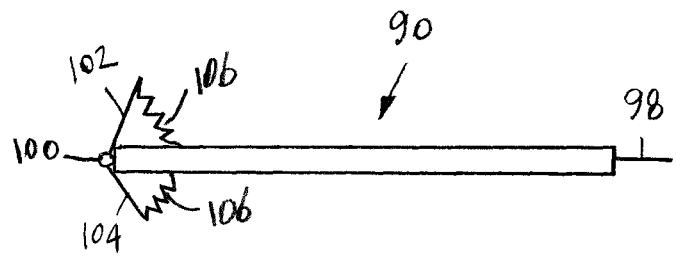
FIG. 7 is a perspective view of the embolic filter device shown in FIG. 6 with the embolic filter device being shown in an expanded state.

With particular reference now to FIG. 7, the embolic filter device 90 is shown in the expanded state. In this particular view, the wire 98 has been pulled to move the tip portion 100 toward the front open end 94. In doing so the arms 102 and 104 open to thereby also open the canopy 106. In this manner, the canopy 106 is capable of capturing and retaining debris. Due to the canopy 106 being constructed of a mesh material, the canopy 106, when expanded, allows blood to flow through.

Figure 8:
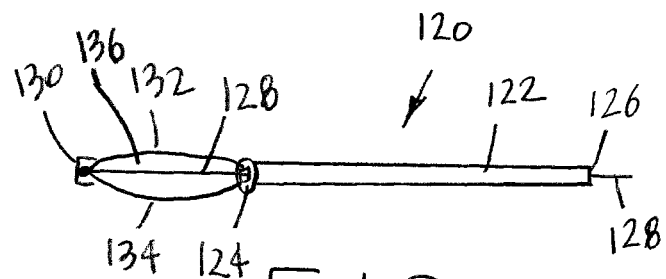
FIG. 8 is a perspective view of another embodiment of an embolic filter device constructed according to the present disclosure with the embolic filter device being shown in a collapsed state.

FIG. 8 shows another embodiment of an embolic filter device 120 constructed according to the present disclosure. The embolic filter device 120 has a catheter portion 122 having a front open end 124 and a rear open end 126. A wire 128 is inserted through the catheter portion 122 and is connected to a capture tip portion 130. The capture tip portion 130 is used to capture therein self expanding arms 132 and 134. The arms 132 and 134 have a mesh canopy 136 connected to the arms 132 and 134.

Figure 9:
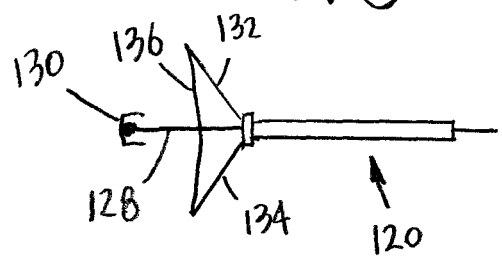
FIG. 9 is a perspective view of the embolic filter device shown in FIG. 8 with the embolic filter device being shown in an expanded state.

Referring now to FIG. 9, the device 120 is shown in an opened or expanded state. In particular, the capture tip portion 130 has been moved forward by moving the wire 128 forward to release the arms 132 and 134 from within the capture tip portion 130. Once released, the arms 132 and 134 are capable of springing outwardly away from the catheter portion 122 to open the canopy 136. In this manner, the canopy 136 is capable of capturing and retaining debris. Due to the canopy 136 being constructed of a mesh material, the canopy 136, when expanded, allows blood to flow through.

Figure 10:
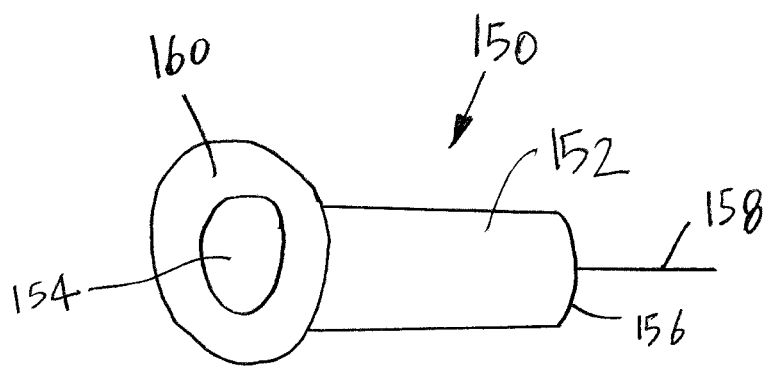
FIG. 10 is a perspective view of another embodiment of an embolic filter device constructed according to the present disclosure.

FIG. 10 shows another embodiment of an embolic filter device 150 constructed according to the present disclosure. The embolic filter device 150 has a mesh central body portion 152 having an open front end 154 and a closed rear end 156. A wire 158 is connected to the closed rear end 156. The open front end 154 also has cuff 160 that is used to allow a catheter or other device to pass by the device 150. Blood and debris are allowed to enter into the device 150 though the front end 154. The rear end 156 will capture or trap any debris and allow blood to flow out through the mesh of the rear end 156. The cuff 160 is sized and shaped to conform to a vessel wall, such as the aorta arch. It is also possible that the device 150 may be constructed without the wire 158.

Figure 11:
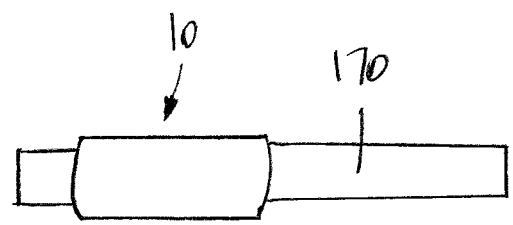
FIG. 11 is a perspective view of the embolic filter device shown in FIG. 1 being placed on a TAVR catheter.

With particular reference now to FIG. 11, the device 10 is shown being placed on a TAVR catheter 170. The device 10 is positioned in the aortic arch 40 (FIG. 1) by use of the TAVR catheter 170. Once in place, the device 10 can be released from the catheter 170 to be deployed or expanded to capture or filter any debris generated during the TAVR procedure. Any of the other embolic filter devices described herein can be placed on the TAVR catheter 170 to be positioned in the aortic arch. Further, instead of using the TAVR catheter 170, a wire or other catheter may be used to position or retrieve the device 10 or the other embolic filter devices. Also, the device 10 or any of the other embolic filter devices can be left in the aorta for continuous filtering or the devices may be recaptured or retrieved whenever it is determined to remove the filters.

Figure 12:
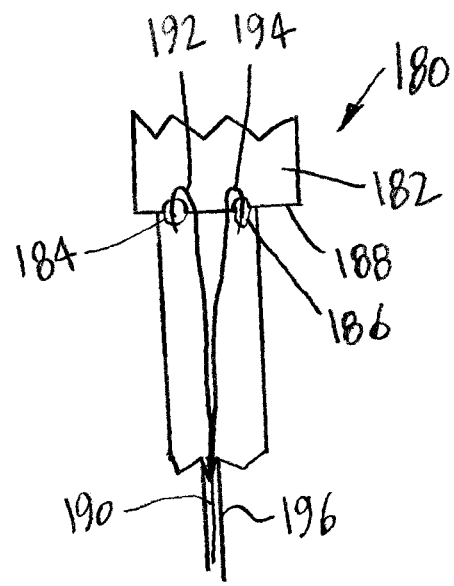
FIG. 12 is a perspective view of another embodiment of an embolic filter device constructed according to the present disclosure.

FIG. 12 shows another embodiment of an embolic filter device 180 constructed according to the present disclosure. The embolic filter device 180 has a central body portion 182 and a pair of rings 184 and 186 extending from a rear end 188 of the device 180. The rings 184 and 186 are used to allow a wire 190 having a pair of hooked ends 192 and 194 to be able to hook to the rings 184 and 186 to remove the device 180 from the aortic arch. The wire 190 having the hooked ends 192 and 194 may be inserted into a removal catheter 196.

Figure 13:
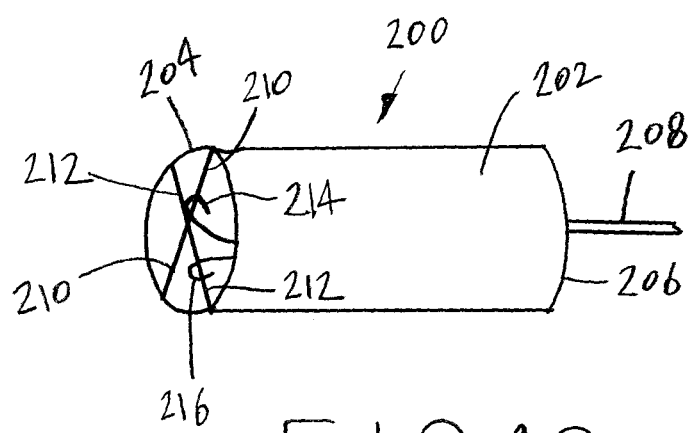
FIG. 13 is a perspective view of another embodiment of an embolic filter device constructed according to the present disclosure.

Further reference is now made to FIG. 13 wherein another embodiment of an embolic filter device 200 is shown. The embolic filter device 200 has a mesh tubular body 202 having an opened front end 204 and a closed rear end 206. A catheter 208 is connected to the closed rear end 206. The opened front end 204 also has a pair of arms 210 and 212, orientated in a cross configuration. The arms 210 and 212 are used to allow a pair of hooked ends 214 and 216 to hook on to the arms 210 and 212 to be able to remove the device 200 from the aortic arch. The hooked ends 214 and 216 are inserted through the catheter 208. In this particular view, the hooked end 214 is attached to the arm 210 and the hooked end 216 is attached to the arm 212.

Figure 14:
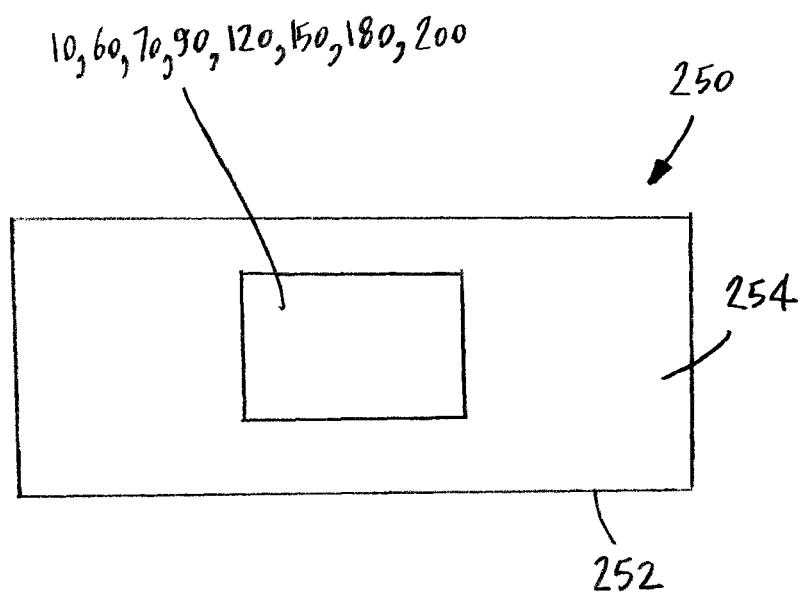
FIG. 14 is a perspective view of another embodiment of an embolic filter device constructed according to the present disclosure.

FIG. 14 is another embodiment of an embolic filter device 250 constructed according to the present disclosure. The device 250 may comprise any of the devices 10, 60, 70, 90, 120, 150, 180, and 200 that have been described and disclosed herein and a stent 252. The stent 252 has an interior 254. The device 250 has been inserted into or positioned within the interior 254 of the stent 252. The stent 252 is collapsible and expandable. The device 250 may be delivered to the aortic arch 40 (FIG. 1).

The devices 10, 60, 70, 90, 120, 150, 180, 200, and 250 can be coated with a coating, such as by way of example only, a heparin coating, to reduce formation of clots. The devices 10, 60, 70, 90, 120, 150, 180, 200, and 250 may also be coated with a drug-eluting coating containing an anti-inflammatory or antistenosis agent. Further, the devices 10, 60, 70, 90, 120, 150, 180, 200, and 250 may be used to protect other organs, such as placing the devices 10, 60, 70, 90, 120, 150, 180, 200, and 250 in the descending aorta to protect the kidneys or other lower extremities. The devices 10, 60, 70, 90, 120, 150, 180, 200, and 250 may be entered into the vascular system via arterial puncture such as femoral, brachial, radial, or etc. Alternatively, the devices 10, 60, 70, 90, 120, 150, 180, 200, and 250 may be inserted via a vein and the across the iter-atrial septum to the left atrium left ventricle, and aorta. The devices 10, 60, 70, 90, 120, 150, 180, 200, and 250 may also be inserted trans hepatic. The embolic filter devices 10, 60, 70, 90, 120, 150, 180, 200, and 250 may be inserted in a low profile collapsed form and expanded within the body once the devices 10, 60, 70, 90, 120, 150, 180, 200, and 250 are in position for deployment. The devices 10, 60, 70, 90, 120, 150, 180, 200, and 250 may then be collapsed prior to removal of the devices 10, 60, 70, 90, 120, 150, 180, 200, and 250 from within the body. As has also been described, the devices 10, 60, 70, 90, 120, 150, 180, 200, and 250 may be left in the body to continuously filter debris and protect against debris or emboli.

From all that has been said, it will be clear that there has thus been shown and described herein an embolic filter device which fulfills the various advantages sought therefore. It will become apparent to those skilled in the art, however, that many changes, modifications, variations, and other uses and applications of the subject embolic filter device are possible and contemplated. All changes, modifications, variations, and other uses and applications which do not depart from the spirit and scope of the disclosure are deemed to be covered by the disclosure, which is limited only by the claims which follow.

What is claimed is:

1. An embolic filter device comprising: a tubular structure having a front end, a first section, a first section rear end, a left collection pocket formed in the first section rear end, a right collection pocket formed in the first section rear end, a first constricted passage, a second section, a second section front end, a second section rear end, a left second section collection pocket, a right second section collection pocket, a second constricted passage, and a rear end.

2. The embolic filter device of claim 1 wherein the device is constructed of a suitable material comprising a polymer, a metal, or a combination of thereof.

3. The embolic filter device of claim 1 wherein the device is configured to be positioned within an aortic arch and configured to expands to form a shape of the aortic arch.

4. The embolic filter device of claim 1 wherein the first constricted passage is closed and is capable of stretching to allow a wire, catheter, or other device to pass through the passage without allowing any debris to pass there through.

5. The embolic filter device of claim 1 wherein the device is formed as a tubular mesh structure.

6. The embolic filter device of claim 1 wherein the first section is larger than the second section.

7. The embolic filter device of claim 1 wherein the first constricted passage comprises a spring.

8. The embolic filter device of claim 1 wherein the first constricted passage comprises a band constructed of polytetrafluoroethylene.

9. An embolic filter device comprising: a tubular structure having a front end, a first section, a first section rear end, a left collection pocket formed in the first section rear end, a right collection pocket formed in the first section rear end, a first constricted passage, a second section, a second section front end, a second section rear end, a left second section collection pocket, a right second section collection pocket, a second constricted passage, and a rear end; and a stent having an interior, the tubular structure for insertion into the interior of the stent.

10. The embolic filter device of claim 9 wherein the first constricted passage is closed and is capable of stretching to allow a wire, catheter, or other device to pass through the passage without allowing any debris to pass there through.

11. The embolic filter device of claim 9 wherein the embolic filter device is constructed of a suitable material as comprising a polymer, a metal, or a combination of thereof.

12. The embolic filter device of claim 9 wherein the first section is larger than the second section.

13. The embolic filter device of claim 9 wherein the first constricted passage comprises a spring.

14. The embolic filter device of claim 9 wherein the first constricted passage comprises a band constructed of polytetrafluoroethylene.

* * * * *

UNITED STATES PATENT AND TRADEMARK OFFICE
CERTIFICATE OF CORRECTION

| | |
|---|---|
| PATENT NO. | : 11,786,354 B2 |
| APPLICATION NO. | : 17/485899 |
| DATED | : October 17, 2023 |
| INVENTOR(S) | : Gil Vardi |

It is certified that error appears in the above-identified patent and that said Letters Patent is hereby corrected as shown below:

In the Claims

In Column 8, Line 3, Claim 3, change "expands" to --expand--.

Signed and Sealed this
Twenty-first Day of November, 2023

*Katherine Kelly Vidal*

Katherine Kelly Vidal
*Director of the United States Patent and Trademark Office*